(12) United States Patent
Birmingham et al.

(10) Patent No.: US 11,620,977 B2
(45) Date of Patent: Apr. 4, 2023

(54) SYSTEM AND METHOD FOR AMBIENT NOISE DETECTION, IDENTIFICATION AND MANAGEMENT

(71) Applicants: Elina Birmingham, Delta (CA); Siamak Arzanpour, North Vancouver (CA); Behnaz Bahmei, Surrey (CA)

(72) Inventors: Elina Birmingham, Delta (CA); Siamak Arzanpour, North Vancouver (CA); Behnaz Bahmei, Surrey (CA)

( * ) Notice: Subject to any disclaimer, the term of this patent is extended or adjusted under 35 U.S.C. 154(b) by 0 days.

(21) Appl. No.: 17/780,917

(22) PCT Filed: Dec. 14, 2020

(86) PCT No.: PCT/CA2020/051721
§ 371 (c)(1),
(2) Date: May 27, 2022

(87) PCT Pub. No.: WO2021/119806
PCT Pub. Date: Jun. 24, 2021

(65) Prior Publication Data
US 2022/0415301 A1    Dec. 29, 2022

Related U.S. Application Data

(60) Provisional application No. 62/950,108, filed on Dec. 19, 2019.

(51) Int. Cl.
*G10K 11/175*  (2006.01)
*G10K 11/178*  (2006.01)
(Continued)

(52) U.S. Cl.
CPC ...... *G10K 11/17854* (2018.01); *A61B 5/6817* (2013.01); *A61B 5/7203* (2013.01);
(Continued)

(58) Field of Classification Search
CPC ......... G10K 11/17854; G10K 11/1752; G10K 11/17823; G10K 11/17873;
(Continued)

(56) References Cited

U.S. PATENT DOCUMENTS

2007/0086599 A1    4/2007  Wilmink
2008/0112569 A1*   5/2008  Asada ............... G10K 11/17833
                                                   381/71.1

(Continued)

OTHER PUBLICATIONS

International Search Report in International Application No. PCT/CA2020/051721 dated Apr. 7, 2021.
(Continued)

*Primary Examiner* — Paul Kim
*Assistant Examiner* — Friedrich Fahnert

(57) ABSTRACT

Examples of system for ambient aversive sound detection, identification and management are described. The system comprises an earpiece device with a microphone configured to capture ambient sound around a user and sample it into small segments of the ambient sound, a speaker and a regulator to regulate the ambient sound segment transmitted to the speaker. The system further comprises a processing unit that identifies aversive ambient sound signals in the captured sound segment and provide recommendation action to manage the aversive sound signal by removing, supressing, attenuating or masking the aversive signals.

28 Claims, 5 Drawing Sheets

(51) Int. Cl.
*H04R 1/10* (2006.01)
*A61B 5/00* (2006.01)

(52) U.S. Cl.
CPC .... *G10K 11/1752* (2020.05); *G10K 11/17823* (2018.01); *G10K 11/17873* (2018.01); *H04R 1/1016* (2013.01); *H04R 1/1083* (2013.01); *G10K 2210/1081* (2013.01); *G10K 2210/3011* (2013.01); *G10K 2210/3027* (2013.01); *G10K 2210/3028* (2013.01); *G10K 2210/3044* (2013.01); *G10K 2210/3047* (2013.01); *G10K 2210/3056* (2013.01); *G10K 2210/30231* (2013.01); *H04R 2460/01* (2013.01); *H04R 2460/11* (2013.01)

(58) Field of Classification Search
CPC ... G10K 2210/1081; G10K 2210/3011; G10K 2210/30231; G10K 2210/3027; G10K 2210/3028; G10K 2210/3044; G10K 2210/3047; G10K 2210/3056; A61B 5/6817; A61B 5/7203; H04R 1/1016; H04R 1/1083; H04R 2460/01; H04R 2460/11
USPC .......................................................... 381/71.6
See application file for complete search history.

(56) References Cited

U.S. PATENT DOCUMENTS

2017/0200444 A1\* 7/2017 O'Connell ....... G10K 11/17885
2020/0312294 A1 10/2020 Isberg et al.

OTHER PUBLICATIONS

Written opinion on Patentability of International Application No. PCT/CA2020/051721 dated Apr. 7, 2021.

\* cited by examiner

SYSTEM AND METHOD FOR AMBIENT NOISE DETECTION, IDENTIFICATION AND MANAGEMENT

CROSS REFERENCE TO RELATED APPLICATIONS

This application is a U.S. National Stage Application of International application No. PCT/CA2020/051721 filed Dec. 14, 2020, which claims priority from U.S. Patent Application No. 62/950,108 filed on Dec. 19, 2019. The entirety of all the above-listed applications are incorporated herein by their reference.

FIELD

This invention generally relates to systems and methods for detecting, identifying/classifying, and managing ambient aversive sounds, particularly intelligence systems and methods for ambient aversive sounds attenuation and suppression.

BACKGROUND

There are several kinds of aversive sounds like industrial and constructional noises known as a hazard to ears that can be harmful when they are too loud, even for a brief time. Every day, many people are exposed to these noises all over the world. A noisy environment during a conversation can be annoying and makes it hard for people to concentrate on another person's speech and may miss important information on the speech. Moreover, some people have reduced tolerance for everyday noises (hyperacusis) and react negatively to very specific noises. Sound sensitivities affect the general public and occur very commonly in the population of Autism Spectrum Disorders (ASD). Negative reactions to sounds can be extremely debilitating, interfering with social interaction, and participation in everyday activities. Therefore, dealing with this issue is an important problem for everyone, especially for people who are sensitive to sound generally and/or specific sounds.

There are known systems and devices which address this problem by using signal processing methods and/or mechanical means. Some of such known systems focus on ear protection by controlling the amount of sound and denoising speech, as taught in US patent application No. 2014/0010378 A1, or by masking the noise by playing music or other specific sounds as disclosed in US patent application No. 20200312294. Many documents such as U.S. Pat. Nos. 9,524,731 B2 and 9,648,436B2 are addressing this issue by extracting particular characteristics from the user's digitized ambient sounds and providing appropriate information to help the listeners' hearing ability or protect them from dangerous sounds.

In some known devices, active noise-canceling technology is implemented to address this problem, such that the incoming sounds from ear-wearing devices are detected and the out-of-phase signals with the aversive signals are generated to cancel the aversive sounds. These active noise cancellation techniques are most effective on lower frequencies and sustained sounds, between 50 Hz and 1 kHz.

The main drawbacks of the existing systems and devices are that they are designed to attenuate or remove all ambient noise, regardless of the nature of the sound. For example, people may want to be aware of the sounds of their children playing while suppressing aversive street noises. Another limitation is that devices that attenuate or cancel ambient noise may limit social communication because the user does not hear speech sounds. Known devices capable of denoising speech in noisy environments are designed for industrial settings where workers wear the same device and communicate through a telecommunications transmission link (e.g., US20160126914A1).

There are also known systems and devices that use multiple microphone techniques located in different spatial locations of the device to suppress the aversive sounds (as taught in the EPO patent application No. EP3096318A1). However, these systems are not practical since, in most cases, these multiple microphone techniques do not succeed at suppressing the target noises, especially when the microphones are capturing the same signals from the surroundings, or they move and shake while the users are doing activities. Moreover, based on the earbuds and headphones' acoustic design, the implementation of the multiple channel microphones and the intelligent algorithms is quite difficult and expensive. On the other hand, newer approaches use single-channel audio to identify and suppress the noises (as disclosed in EPO Pat. No. EP3175456B1). Systems and methods in real-world applications based on single-channel audio identification and noise suppression are effectively practical, but such systems have quality and accuracy limitations.

Therefore, a system and method that is noise-content-aware to filter specific user-defined ambient noise are needed instead of systems that equally treat all ambient noise.

SUMMARY

In one aspect a system for ambient aversive sound detection, identification and management is provided. The system comprises an earpiece device that has a microphone configured to capture ambient sound around the user as samples of small segments of the ambient sound and a speaker; an interface with a hardware processor that is programmed with executable instructions to obtain input data, transmit data and provide output data; a memory unit to store input information, a library of aversive ambient sound signals, aversive sound feature maps, identifying prediction models, aversive sound identifying classes, and aversive sound suppression prediction models; and a processing unit in communication with the earpiece device, the memory unit and the interface. The processing unit comprises an identifying unit that is coupled to the earpiece device and the memory unit and a filtration processing unit that is coupled to the identifying unit and the memory unit. The identifying unit is programmed with executable instructions to identify an aversive ambient sound signal in the ambient sound segment by extracting at least one feature of the sound in the sound segment and create a feature map of such sound segment. The feature map of the sound segment is processed using the identifying prediction model stored in the memory unit to compare at least one feature in the feature map with the feature maps of aversive sound signals stored in the memory unit and when the aversive ambient sound is identified the identifying unit categorizes the aversive sound signal with an identifying class. The filtration processing unit is programmed with executable instructions to receive a mix-signal of ambient sound segments with aversive sound signal from the identifying unit and process the mix-signal computing an amplitude and phase of the mix-signal to generate a feature map of the mix-signal, compare the feature map with the stored feature maps using at least one aversive sound suppressive model and provide a recommend action to manage such aversive sound signals. The earpiece device further comprises a valve to regulate the ambient sound segment transmitted to the user.

In one aspect, the recommended action is to remove the aversive sound and the filtration processing unit is further programmed with executable instructions to automatically remove the identified aversive signals from the mix-signal using the generated feature map to obtain a clean sound of the mix-signal which is reconstructed from a frequency domain to a time domain, and to combine a phase of the mix-signal with amplitudes of the clean sound for the last segments to create a clean sound signal that is transmitted to the speaker.

In another aspect, the recommended action is to attenuate the aversive sound and the filtration processing unit further comprises a bypass with a gain to create an attenuated aversive sound. The filtration processing unit is programmed with executable instructions to automatically add the attenuated aversive sound signal to the clean sound signal.

In yet another aspect, the filtration processing unit is programmed with executable instructions to automatically add the pre-recorded sound over the mix-signal to mask the aversive ambient sound signal.

In one aspect, the system comprises a first activation device in communication with the earpiece device to manually trigger the valve to suppress or attenuate the aversive ambient sound signal and a second activation device in communication with the earpiece device and the memory unit to manually access the stored pre-recorded sounds and play them over the mix-signal to mask the aversive ambient sound signal.

In one aspect, the system comprises an alert system in communication with the interface and/or the earpiece device to generate an alert signal to alert the user of the recommendation action. The alert signal is selected from one of a visual, tactile, sound signal or any combination thereof.

In another aspect, the system comprises at least one physiological sensor in communication with the processing unit that is configured to detect at least one physiological parameter of the user. The processing unit identifies the aversive ambient sound signal in the ambient sound segment if the detected parameter is outside a pre-determined range of the at least one of the detected physiological parameter.

In one aspect a method for ambient aversive sound detection, identification and management is provided. The method comprises capturing a stream of ambient sound segments using a microphone in an earpiece device; storing input information, a library of aversive ambient sound signals, aversive sound feature maps, identifying prediction models, aversive sound identifying classes and aversive sound suppression prediction models on a memory unit; and processing the captured sound segments by a processing unit. The processing step comprises extracting at least one feature of the sound signal in the sound segment, creating a feature map of the sound segment, comparing the at least one feature in the feature map with the feature maps of aversive sound signals in the identifying prediction model stored in the memory unit, identifying an aversive sound signal in the captured sound segment using the identifying prediction model and categorizing the identified aversive sound signal with an identifying class; and filtration processing of a mix-signal that comprises the ambient sound segments with the aversive ambient sound signal, computing an amplitude and phase of the mix-signal to generate a feature map of the mix-signal, comparing the feature map with the stored feature maps using at least one aversive sound suppressive model and providing a recommend action to manage the aversive sound signals.

In addition to the aspects and embodiments described above, further aspects and embodiments will become apparent by reference to the drawings and study of the following detailed description.

DETAILED DESCRIPTION

Embodiments of this invention provide device details, features, systems, and methods for ambient aversive sounds detection and identification/classification, as well as systems and methods for ambient aversive sounds isolation and suppression.

Figure 1:
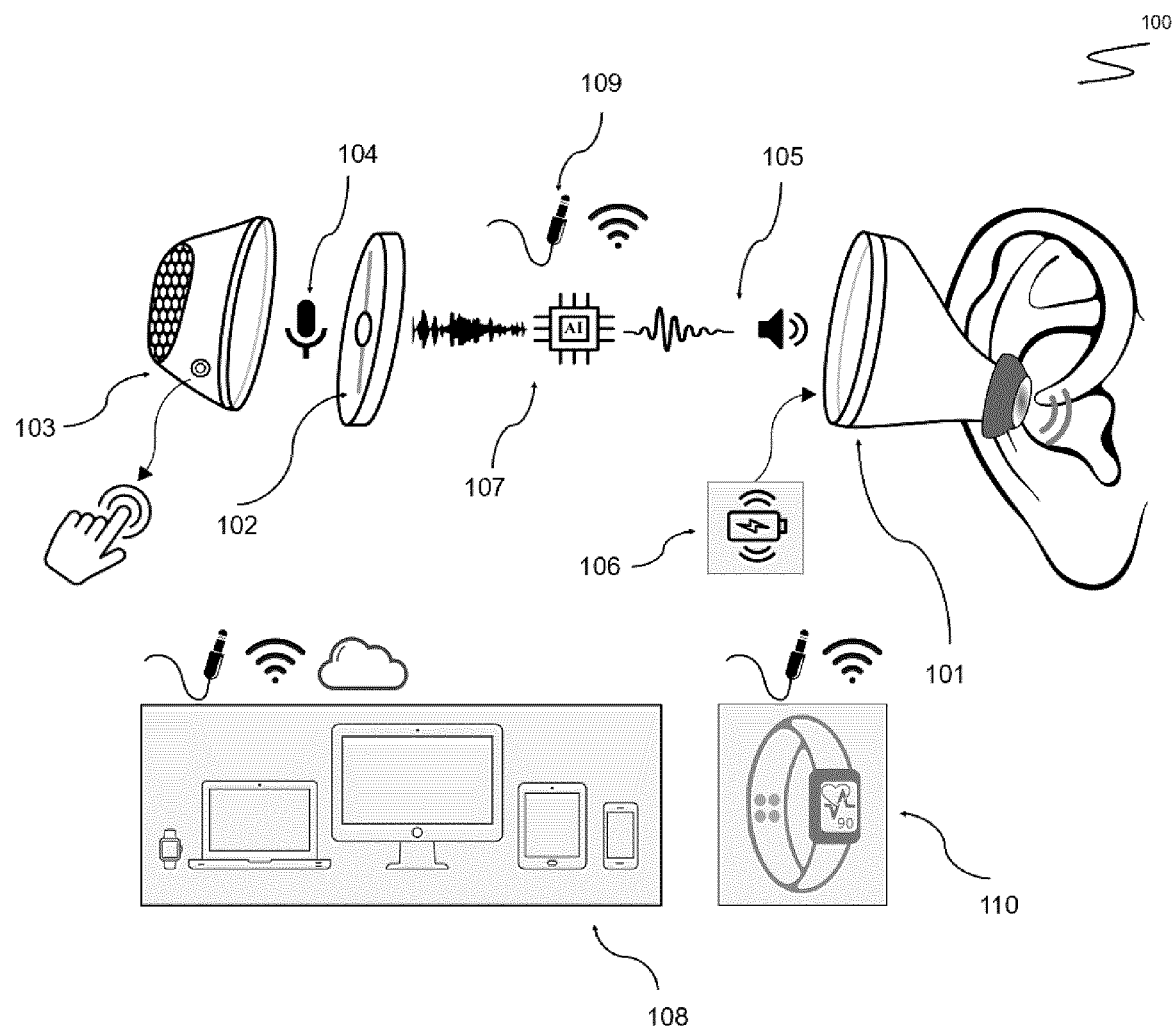
FIG. 1 shows an exemplary schematic of a system for detecting, identifying, and managing ambient aversive sounds.

FIG. 1 shows a schematic example of a system 100 for detecting, identifying/classifying, and manage ambient aversive sounds. The system 100 comprises an earpiece device 101, such as a set of earplugs or earmuffs, with a microphone 104. In some embodiments, the system 100 can also be equipped with a speaker 105 and/or a valve 102. The valve 102 can suppress or isolate the ambient sound. The valve 102 can be opened or closed, such that when the valve is in "open mode", ambient sounds can pass through system 100 slightly attenuated due to the material's passive noise isolation in the earplug or earmuff and when the valve 102 is in "closed mode," the ambient sounds can be attenuated or isolated. In one embodiment, the valve 102 can be activated/deactivated electronically using a solenoid, voice coil, etc. For example, an activation button 103 can be used to operate the valve 102. The button 103 can be placed somewhere on the earpiece device 101 or positioned on a wearable or handheld device 108, 110 and the electronic triggering signal can be transferred by wire or wirelessly to the activation device 103. The activation device 103 can be any known mechanic or electronic activation mechanism. In another embodiment, the device does not contain a valve, and the device 101 may consist of standard in-ear buds or over-the-ear headphones each equipped with a microphone and speaker, and the system 100 can performs the classification and sound management operations as described herein below.

The system 100 further comprises a processing unit 107. The processing unit 107 can be positioned in the earpiece device 101, or it can be positioned outside the earpiece device 101. For example, the processing unit 107 can be in a smart wearable 110 or a handheld device 108 (e.g., mobile phone, tablet, laptop) or any other suitable smart device. In one implementation, the processing unit 107 can be in a hardware server or virtual server (cloud server) that is in communication with the earpiece device 101 using internet communication. In one embodiment, one part of the processing unit 107 can be in the earpiece device 101 and another part in the smart wearable/device or any other computer or server. The processing unit 107 can comprise a memory unit, such as a non-transitory memory, storing data, an identifier or classifier models and instructions (FIG. 3), and a filtration processing models and instructions (FIG. 4). The system 100 can further comprise a user interface 500 shown in details in FIG. 5. The user can provide input data to the system 100 through the interface 500. The memory unit stores the input data, captured ambient sound data, a library of known ambient sounds, sound feature maps as well as prediction models used by the classifier 300 and the filtration processor 400.

Figure 2:
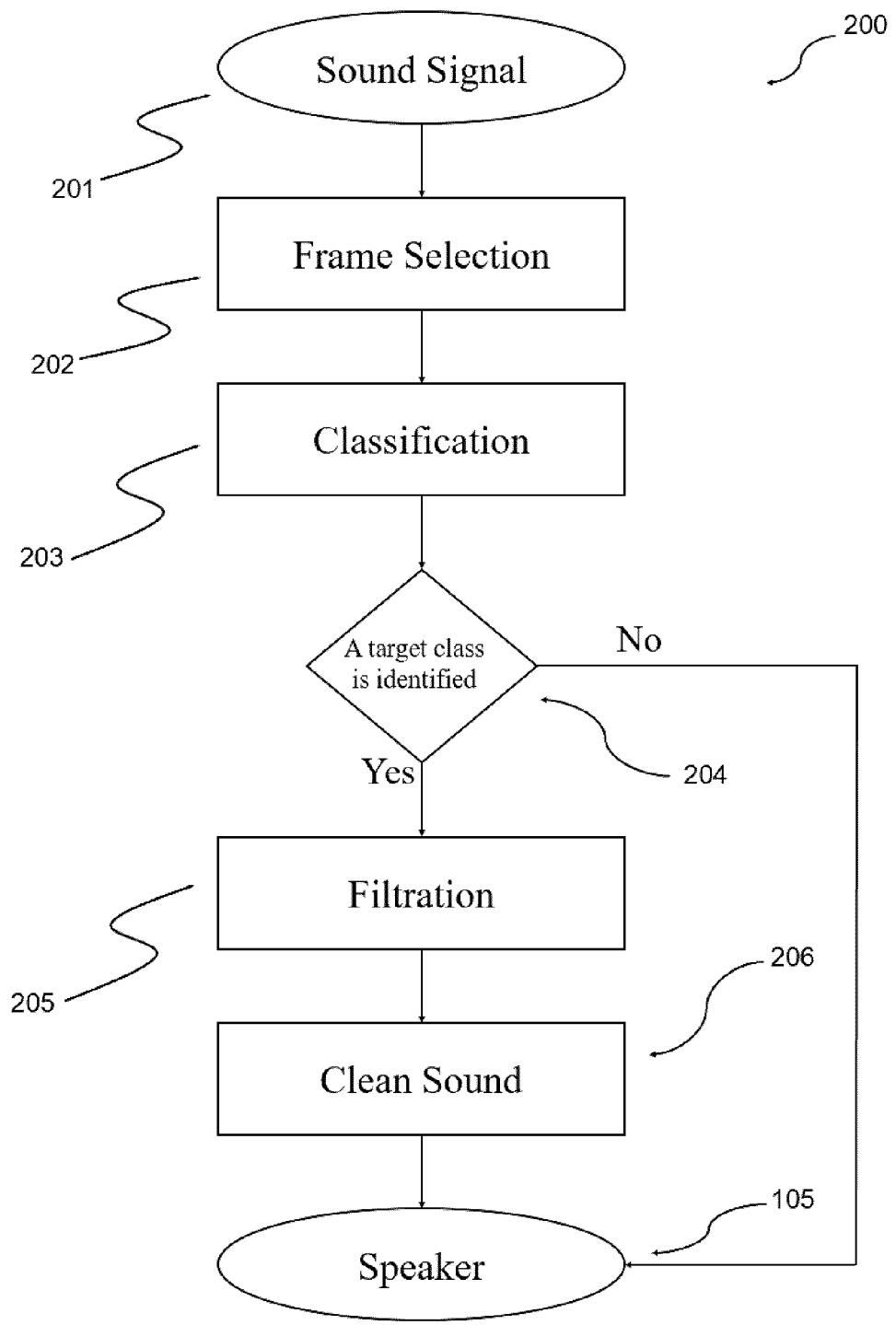
FIG. 2 shows a simplified block diagram of an example of a method for detecting, identifying/classifying, and managing ambient aversive sounds according to one embodiment of the present invention.

FIG. 2 illustrates the overall steps 200 performed by the system 100 to detect, classify, and manage aversive ambient sound. The microphone 104 of the earpiece device 101 captures the surround sounds 201 and can play such sounds to the speaker 105. When the device operates in "normal" mode (the valve 102 is in the "open mode", or the speaker plays the undistorted ambient sound captured by the microphone), the user can hear the ambient sound. When an aversive ambient sound is detected, the system 100 is activated, and the system 100 can make recommendation actions such as to either (1) suppress the detected sound that includes the aversive ambient sound by activating the valve 102 so that the device operates in "closed mode", and the valve/plug blocks ambient aversive sound from entering the ear canal, independent of the other operations; (2) suppress the signal by stopping the transfer of the surround sound from the microphone to the speaker 105; (3) attenuate the ambient sound by lowering the volume so that the earphones' headphones play the sound at a reduced volume (user chooses the volume or there is a predefined lower volume); (4) remove the aversive part of the surround sound using the system 100 as described below, or (5) mask the ambient sound by playing pre-recorded sounds to the speaker 105 as an extra masking feature (e.g, playing music, white noise, or any preferred sound by the user). By playing music, white noise, or other preferred sounds during the closed mode, the system 100 can maximally mask the ambient sound beyond what the passive isolation (options 1 and 2) can provide. When the aversive sound is not detected anymore, the system's operation will go back to "normal" mode. The microphone 104 can be mounted outside of the earpiece device 101 and can capture ambient sounds. The microphone 104 is configured to capture a sample of small segments of a sound stream which is considered as a frame selection 202. A frame size is chosen such that the human auditory system cannot understand the associated delay for processing, decision making, and aversive sound suppression for each sound segment/frame. Human ears can tolerate a latency between 20-40 ms and the system 100 is configured to have the latency in this range to work smoothly in real-time. For example, a 24 ms frame size can be used, and the microphone 104 can capture a 24 ms sound frame each time with an 8 Khz sampling rate. In this setting, a segment of the signal 201 consists of 192 data samples.

The ambient sound segment enters as an input in the processing unit 107, where it is processed to identify if the signal segment comprises an aversive sound. As mentioned herein before, the processing can be done in the earpiece device 101, or remotely in a smart wearable 110 or a handheld device 108 (e.g., mobile phone, tablet, laptop) or any other suitable hardware server or virtual server (cloud server) that is in communication with the earpiece device 101 using internet communication. The processing unit 107 comprises an identifier/classifier 203 with a prediction model that is either trained or will be trained to detect and identify aversive sounds that can be predefined by the user or can be aversive sounds previously unheard by the user. The classifier 203 can determine if the ambient sound segment comprises an aversive ambient sound using the classifying prediction model and an aversive sounds library. If the classifier 203 does not identify any aversive sound in the sound segment then such signal is transferred to the speaker 105 and the user can hear it. If the classifier 203 identifies that the ambient audio segment comprises an aversive sound 204, a mix-signal of the ambient audio segment with the aversive sound is processed by the filtration processor 205 where particular features of the mix-signal are determined for aversive sound suppression purpose using the aversive sound suppression prediction model. In one implementation of the system 100, the processing unit 107 can use the result of the filtration processor 205 to automatically remove or suppress the aversive sound signal from the mix-signal resulting in a clean sound 206 as an output. The clean sound 206 can then be played in the speaker 105, positioned in the earpiece device 101, e.g., the headphone or earphone.

In one implementation, the processing unit 107 can provide recommendation action to the user. For example, the processing unit 107 can send an alert with the recommendation action using the interface 500. The recommendation action can be, for example, (1) suppress the sound signal by closing the valve 102, or (2) suppress the signal by stopping the transfer of the signal from the microphone to the speaker, or (3) attenuate the ambient sound by lowering the volume, or (4) remove the aversive sound signal from the mix-signal, or (5) mask the ambient sound by playing pre-recorded sounds. The user can then decide and manually execute the recommended action using the interface 500 or activation device 103 or a plug in some implementations. In another implementation, the system can automatically trigger the valve or activation device to suppress or attenuate the signal, or to activate a player storing the pre-recorded masking sounds, or provide instruction to the processing unit 107 to remove the aversive sound from the signal.

The masking sound can be pre-recorded and stored in the memory unit, or a separate player storing the pre-recorded sounds can be provided in communication with the earpiece device 101 that can be triggered manually by the user or automatically by the system 100. In one embodiment, the masking sounds can be stored in an app, such as for example Spotify™ and access manually by the user or automatically by the system 100. In embodiments where the system 100 automatically suppresses, attenuates, removes, or masks aversive ambient sound(s), the users can have the ability to override the system's recommendation actions by manually deactivating and activating the system 100 using, for example, the interface 500. The system 100 can continuously monitor the surrounding sounds and samples new sound segments and processes such segments to identify aversive ambient sounds and suppresses, attenuates, removes or masks the aversive sound(s) accordingly as described hereinabove.

The graphical user interface 500 (FIG. 5) can be compatible with every operating system run on the smart wearables or handheld devices 108, 110. The interface 500 has a hardware processor programmed with executable instructions for obtaining input data, transmitting data, and providing output data. For example, the graphical user interface 500 can be responsible for all communications, settings, customizations, and user-defined operations. The computational procedures including artificial intelligent prediction models, models' training, data sampling, data processing, are conducted by the processor 107 that can be in the earpiece device 101, or any of the devices 108, 110 or on a server that is connected to the system by internet network or any combination thereof. The system 100 can further comprise a chargeable battery 106 which supplies the required power for the earpiece device 101. The battery can be charged using a complimentary charger unit.

In one implementation, the system 100 can further comprise a set of physiological sensors to capture bodily reactions. e.g. skin conductance, heart rate, electroencephalography (EEG), electrocardiography (ECG), electromyography (EMG), or other signals. These sensors can be embedded on wearable devices 110 or any other smart device 108 or attached to the user's clothing or body. The provided sensor data will be transferred to the system 100 using the wireless or wired connections 109 to determine bodily reactions. For example, a heart rate monitor can be used to detect the user's heart rate and the processing unit 107 can process such signals to determine stress state of the user, such as for example, the increased heart rate may be a signal that the stress level of the user is increased, or skin conductance monitors can detect increased level of user's physiological arousal. Such bodily reactions may be a result of the aversive ambient sound, so the system 100 can automatically recommend proper actions to be performed accordingly as described herein.

In some embodiments, the system 100 is programmed and comprises algorithms/models that can discriminate and suppress some aversive sounds. The models can be based on machine learning, deep learning, or other techniques of sound detection/identification and suppression.

Figure 3:
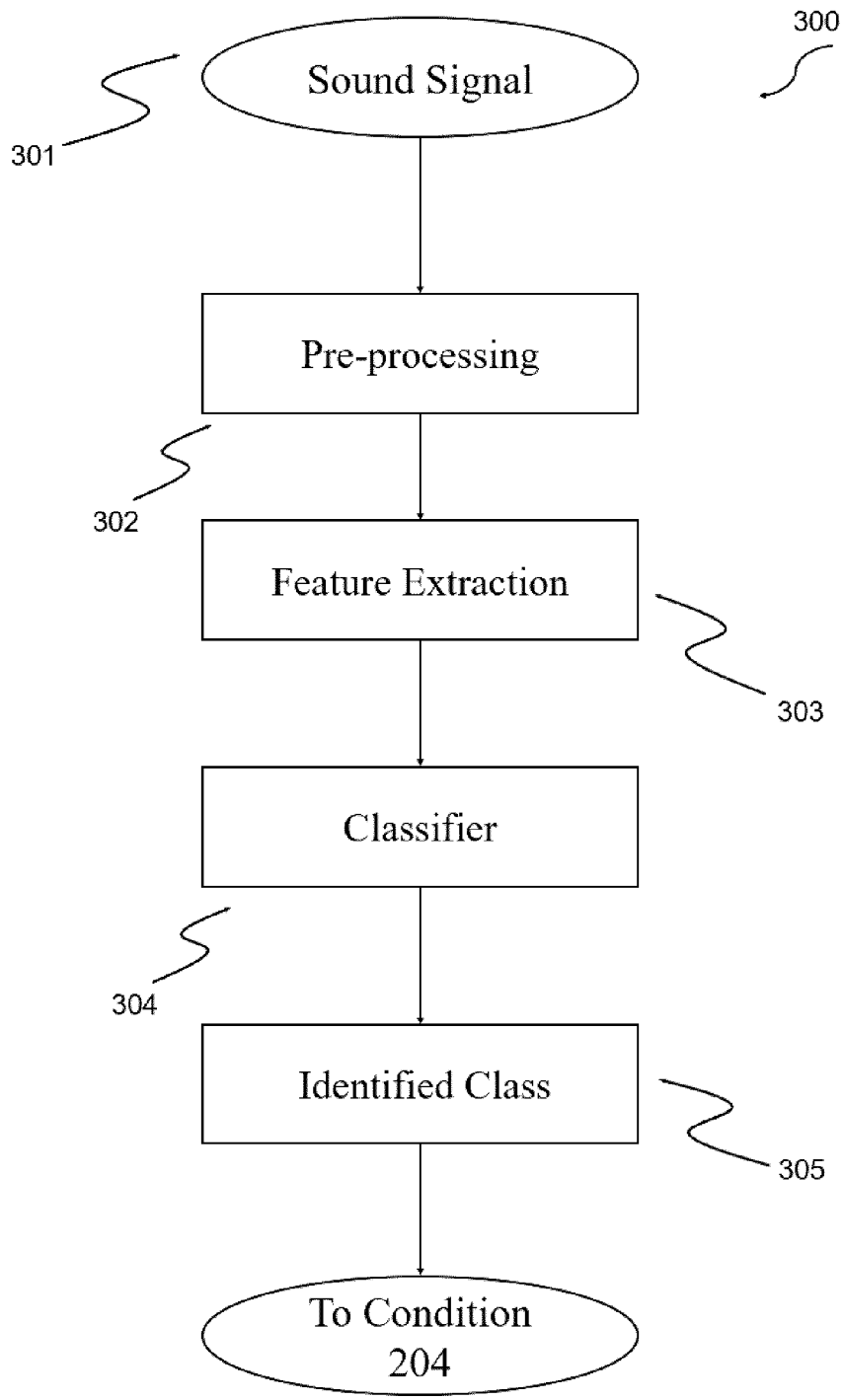
FIG. 3 shows a simplified block diagram of an example of an identification/classification method according to one embodiment of the present invention.
Figure 4:
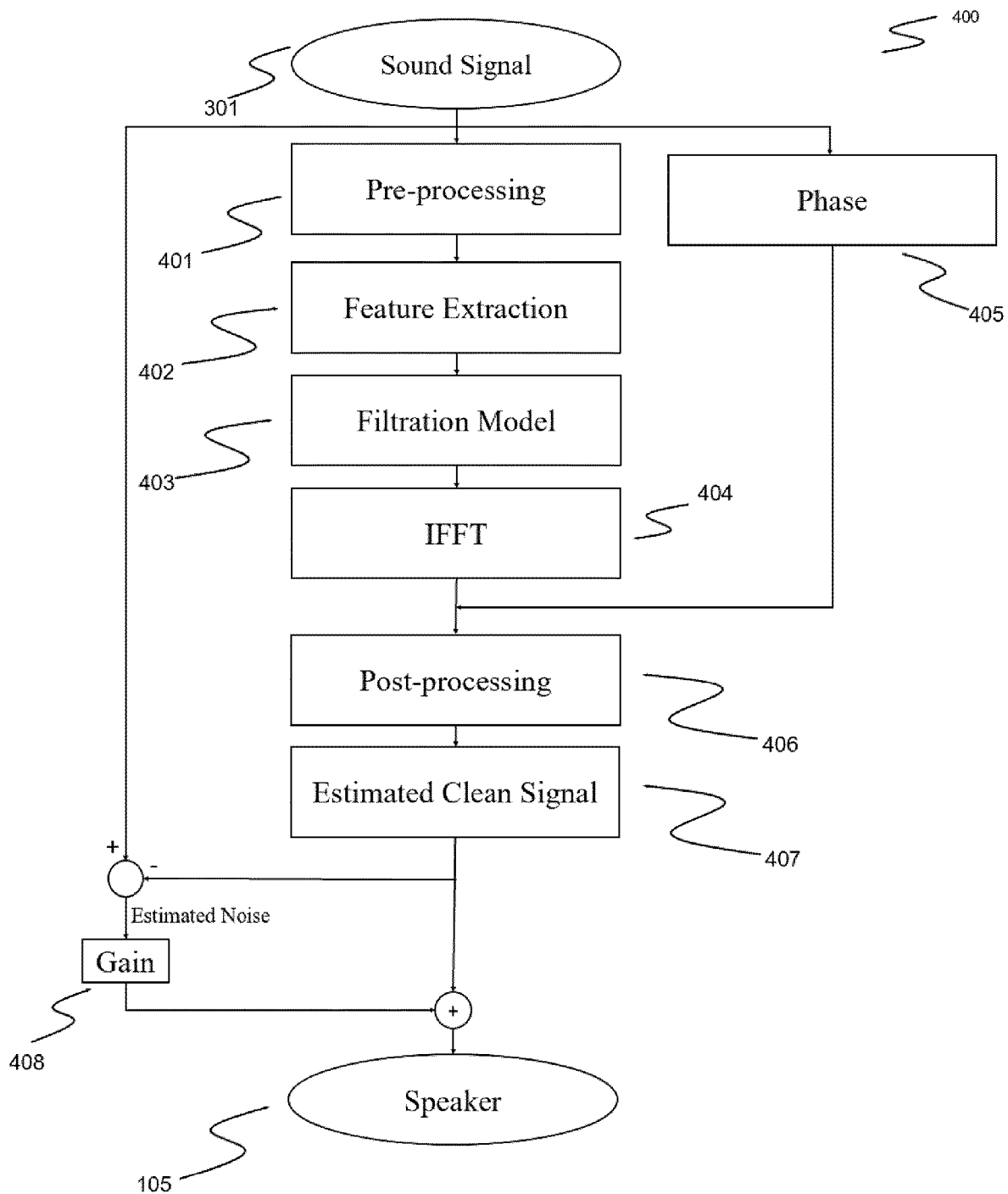
FIG. 4 shows a simplified block diagram of an example of real-time aversive sounds filtration and processing method according to one embodiment of the present invention.

FIG. 3, illustrates an example of an identifier/classifier 203 and a method 300, conducted by the classifier 203. The classifier receives as an input the segmented ambient sound signal 301 obtained from the microphone 104. The signal 301 is then pre-processed in a step 302 to flatten or to create a representation of the signal in the frequency domain by using a Fast Fourier Transform (FFT) of the signal. For example, the pre-processing step can also include signal processing operations (e.g., normalizing, converting sampling rate, windowing, FFT, flattening) to provide inputs to the classifier prediction models (e.g., deep neural network, support vector machine (SVM), linear regression, perceptron, etc.) for aversive sound detection/identification. Then predetermined features are calculated/extracted in step 303 using, for example, the Mel-frequency Cepstrum Coefficient (MFCC), Short-Time Energy (STE), etc. For example, an intensity and power (i.e., the amplitude and frequency) of the signal 301 are extracted, and a feature map 303 is created and input in a classifier prediction model 304. The classification prediction model is a pre-trained model which, in one example, is an artificial neural network comprising a number of hidden layers (e.g., Dense layer, GRU layer, etc.) for learning procedure. The classification prediction model is trained on comprehensive sets of aversive sound classes and consequently, each aversive sound class has a corresponding class number. The feature map 303 is fed to the model 304 and an output 305 is a class number based on the similarity between the signal 301 and the sounds patterns in the library. The identified class can be a number identifying a particular aversive sound. For example, class number 2 can be an air conditioner sound, while a class number 7 can be, for example, a siren, etc. In one implementation, the identification class 305 can be a verbal text.

In one embodiment, if the identifier/classifier identifies an aversive sound in the ambient sound, the user is informed using the graphic interface, and he/she can choose either to use the system 100 to automatically close the valve, suppress, attenuate, or remove the aversive sound and play the rest of the ambient sound into the earphone, or to play music, white noise or any preferred sound or even a combination of the music and the suppressed ambient sound. The user can customize the device to action any of the aforementioned operations and these operations can also change while the aversive sounds are identified based on the user's decision on the sound aversiveness. The mix-signal comprising ambient aversive sound identified with the identified class 305 is then inputted into the filtration processor 204.

FIG. 4 illustrates an example of the filtration processor 204 and a method 400 conducted by the filtration processor 204. In one embodiment, the filtration processor is activated when the classifier identifies an aversive sound in the ambient sound environment. Therefore, input 301 is the mix-signal of ambient sound, which includes an aversive sound. The filtration processor 204 takes a segment of the mix-signal as an input frame and computes the signal's amplitude and phase. The amplitudes are then pre-processed as shown in step 401 to construct a feature map 402 that is used as input to the aversive sound suppression prediction model afterward. For one example, the pre-processing includes taking the FFT of the signal, spectrum analysis, and mathematical operations to create the representation of the mix-signal in the frequency domain as a feature map. The pre-processing step in the filtration process can be different rather than the identification process due to different purposes they have. In one embodiment, the filtration processor 204 can take several overlapped chunked frames of the mix-signal and perform pre-processing to calculate the power and frequencies in the mix-signal and to construct a feature map. For example, the pre-processing can include signal processing operations to provide inputs to the aversive sound suppression model 403 (e.g. deep neural network, SVM, linear regression, perceptron) for aversive sound suppression. The aversive sound suppression model 403 can be trained to take the flattened (pre-processed) feature map and remove the identified aversive components of the input mix-signal 301. This results in a clean sound of the input mix-signal. The clean sound is in the frequency domain so need to be reconstructed into a clean sound in the time domain by using, for one example Inverse Fast Fourier Transform (IFFT) 404, and the phase 405 of the mix-signal extracted from the original mix-signal 301 is combined with the amplitudes of the clean sound to create a clean signal. In one embodiment, post-processing tools 406 including powering and flattening can be applied to the clean signal to make a smooth clean signal. For example, in one embodiment, the post-processing tools 406 can generate a time domain of the clean sound using the overlap-add method, which can be performed in real-time. As said previously above, the frame size of the captured ambient signal is chosen such that the human perception ability cannot understand the associated delay for processing, decision making, and aversive sound suppression for each sound frame. Human ears can tolerate a latency between 20-40 ms and the system 100 can have the latency in this range to work smoothly in real-time. For example, the microphone 104 captures a 24 ms frame each time with an 8 Khz sampling rate, so that the segment of the signal consists of 192 data samples. Considering the 50% overlap for the overlap-add method, the post-processing tool 406 adds 12 ms overlapped clean signal which is played to the speaker 105. The overlapped technique provides the advantage of smooth continuous framing, and keeps the information at the edge of the frames, to generate a clean, smooth, and continuous sound without the loss of sound quality. Therefore, the output of the post-processing 406 can be the estimated clean signal 407.

Aversive sounds can be considered in three fundamental categories (identified class 305 of FIG. 3) regarding their inherent structures and patterns. These categories include stationary noises like an air conditioner, engine; non-stationary noises like train, wind; and highly dynamic noises like dog barking, siren, and baby crying. In one embodiment, depending on which aversive sound category is identified, the system and method can perform different pre-and post-processing on the mix-signal 410. For example, a digital signal processing filtering aid like an adaptive filter is applied to the non-stationary class noises. For one embodiment, the filtration processor 204 can comprise a number of different aversive sound suppressive models to choose between based on the identified category/class of the aversive sound in order to generate the clean sound. The models for aversive sound suppression are trained on comprehensive datasets resulting in accurate, high performance, and using reliable deep neural network models or other machine learning models.

In one embodiment, the filtration processor 204 comprises an aversive signal bypass 408 configured to attenuate the aversive sound and add the attenuated aversive sound to the clean sound. For example, the users can choose the attenuation level of the aversive sound using settings 506 in the interface 500. In some implementations, the user can manually attenuate the aversive sound level using the slider 505 in the interface 500. The bypass 408 with a gain is considered and multiplied to the estimated aversive signal, which is the subtraction between the mix-signal and the estimated clean signal, to create an attenuated aversive signal. Afterward, this signal is added to the clean signal so that the user can hear the attenuated aversive sound with the clean sound through speaker 105. The level of attenuation which is from zero to maximum attenuation in the bypass gain 408 can be set in the settings or using a designed knob, slider, or button in the user interface 500.

Figure 5:
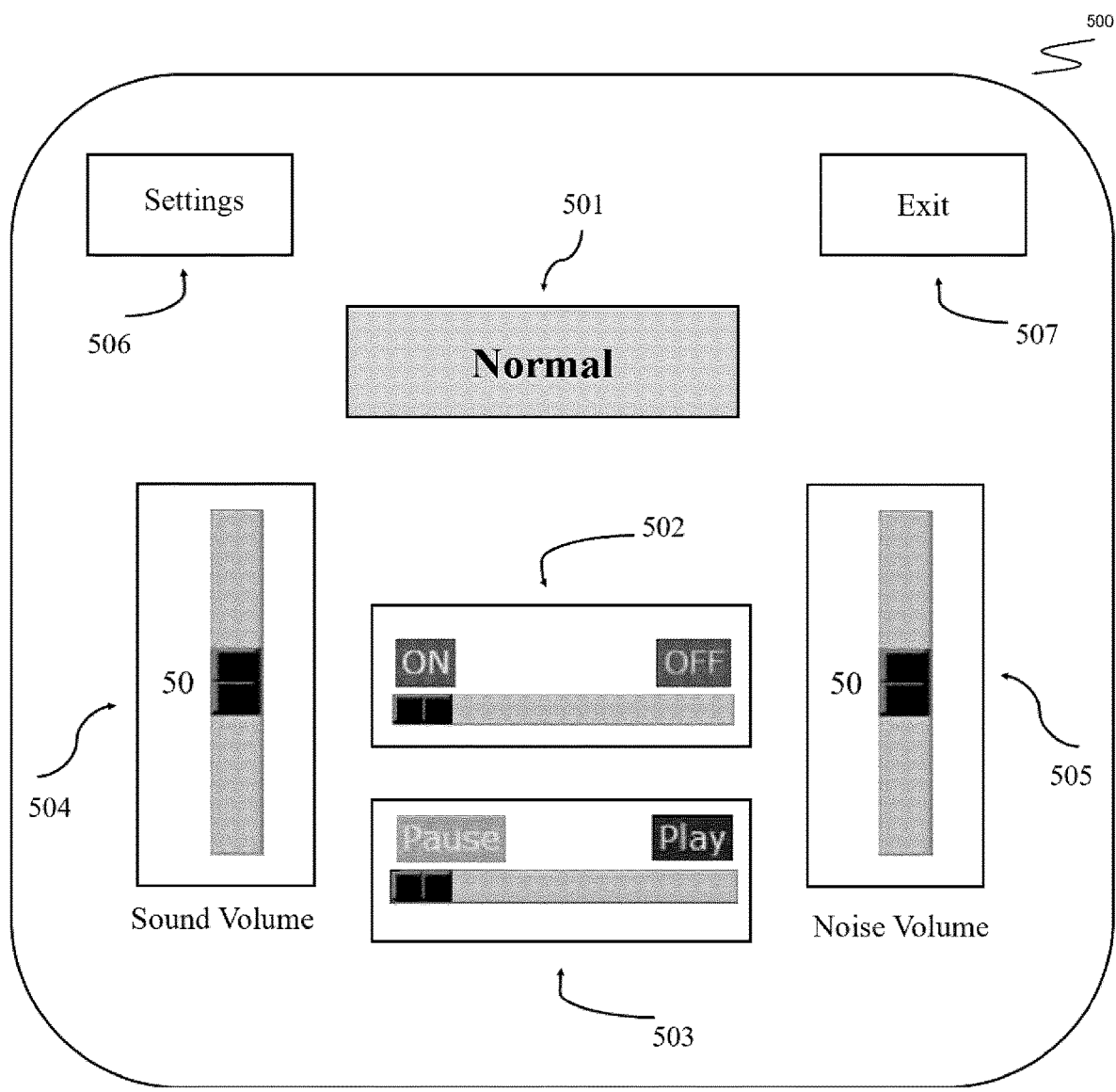
FIG. 5 shows an example of a graphical user interface according to one embodiment of a system for detecting, identifying, and manage ambient aversive sounds.

FIG. 5, illustrates an example of the graphical user interface 500 of the system 100. The graphical user interface 500 can be installed on any smart device, including smartphones, smartwatches, personal computers on any suitable operating system such as IOS, Windows, Android, etc. The installed user interface can interact with the earpiece device 101 using a wired or wireless connection. In the illustrated example shown in FIG. 5, a screen 501 can indicate the system operation mode. For example, the operation modes can be, "normal mode", referring that there is no aversive sound identified by the system and method, and "aversive mode", referring to an aversive sound being identified by the system and methods. In addition, the screen 501 can be used to alert the user of the action recommended by the processing unit 107, such as for example suppress, attenuate or mask the sound. An activation slider 502 is configured to manually turn on and off the system 100. The user can activate the recorder or access the music storing device using a slider 503. The user can play and pause music, white noise, or any preferred sounds based on the surrounding situation or their preferences. In addition, the user can control the volume of the incoming sound to the earphones using a slider 504. In case when an aversive sound is identified and the user is informed, the user can use a slider 505 to selectively attenuate the identified aversive sound. The settings 506 are configured for users' customizations, such that users can input their pre-set preferences, such as for example, choosing and uploading preferred music/sounds to store in the memory unit or a separate recording unit, choosing the alerting setting (e.g., sound alert, or any alert signal such as light, or vibration, or text), choosing an alerting sound, specifying the action(s) to be performed when the aversive sound is identified (e.g., automatic aversive sound management or manually aversive sound management), a check-list of the aversive sounds to be suppressed and/or notified, a button to activate a single-shot learning process. The interface 500 can further comprise an exit button 507 to close the entire program. For the embodiments without the setting in FIG. 5, the process of customization can happen using a personal computer, laptop, smartphone, etc. A user can complete the process of customization as explained previously by logging into a website or a specialized interface provided to them, and after completion, the final setting can be transferred in the earpiece's memory, cloud server, etc., for the processing unit's implementation.

In one embodiment, the alerting system is used to notify the user of the existence of an aversive sound while the system 100 automatically suppress, attenuate or mask such aversive sound. When the system 100 recognizes a nearby aversive sound (e.g., sound that is user-defined as aversive), he/she is notified through the alerting system about such aversive sounds by playing a piece of specific music, white noise, an alert voice, or a light alert (e.g., colored LED), or a text message, a beep in the earpiece device, a vibration, etc., or any combination of these alerts. Users can also be notified about the nature and intensity of the aversive sounds and the recommended actions, such as for example, suppress, attenuate or mask or any combination thereof. The user can override any of the recommendation actions using the interface 500 or an override button on the earpiece. The alert system can be set-up in the interface 500 and can communicate with the user using any smart wearable, handheld device, or earpiece device. The alerting system can be user-customized. The system can also notify the user of the clearance of the aversive sound.

In one embodiment, the user can add user-customized aversive sounds for the system to detect and manage. The system 100 in such embodiment can start with a predefined list of aversive sounds, but when the user hears an aversive sound which is not predefined, he/she can activate the system 100 to record the ambient sound and situation (taking a proper sample of the sound and situation), process the sounds to identify individual components (offline or online), communicate with the user about the findings, and ask the user to specify which one of the identified sounds was aversive, and finally add the aversive sound to a customized library of user's aversive sounds list. In one embodiment, the learning components can be based on one-shot or few-shot learning methods or other intelligent based algorithms like machine learning and deep learning. For example, the system can record the surrounding sound and time stamp the events. Then the user will be notified in real-time or offline about the recorded sounds and be asked to identify the aversive sound by either remembering the sound/situation from the time of the event or by listening to the sample. If the user identifies such sound as aversive, it will be added to the library of aversive sounds.

In one embodiment, the physiological sensors can be used to detect aversive situations from the user's physiological signals, e.g., skin conductance, heart rate, EEG, ECG, EMG, or other signals. These signals (independently or fused) can be used to identify the occurrence of aversive sounds/situations, and the methods explained before can be used to identify the aversive sound component in the mix-signal. Upon the detection of such aversive sound, it can be added to the library of aversive sounds, and the system can take recommended action to attenuate/filter/mask/block such aversive sound. The user will be notified as explained above, and he/she can manually override the recommended action. The aversive component of the sound can be detected and reported to the user for verification before adding it to the library and/or implementing the recommended action.

While particular elements, embodiments and applications of the present disclosure have been shown and described, it will be understood that the scope of the disclosure is not limited thereto, since modifications can be made by those skilled in the art without departing from the scope of the present disclosure, particularly in light of the foregoing teachings. Thus, for example, in any method or process disclosed herein, the acts or operations making up the method/process may be performed in any suitable sequence and are not necessarily limited to any particular disclosed sequence. Elements and components can be configured or arranged differently, combined, and/or eliminated in various embodiments. The various features and processes described above may be used independently of one another or may be combined in various ways. All possible combinations and sub-combinations are intended to fall within the scope of this disclosure. Reference throughout this disclosure to "some embodiments," "an embodiment," or the like, means that a particular feature, structure, step, process, or characteristic described in connection with the embodiment is included in at least one embodiment. Thus, appearances of the phrases "in some embodiments," "in an embodiment," or the like, throughout this disclosure are not necessarily all referring to the same embodiment and may refer to one or more of the same or different embodiments.

Various aspects and advantages of the embodiments have been described where appropriate. It is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without operator input or prompting, whether these features, elements and/or steps are included or are to be performed in any particular embodiment. No single feature or group of features is required for or indispensable to any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The example results and parameters of the embodiments described herein are intended to illustrate and not to limit the disclosed embodiments. Other embodiments can be configured and/or operated differently than the illustrative examples described herein.

The invention claimed is:

1. System for ambient aversive sound detection, identification and management, the system comprising:
   an earpiece device comprising a microphone configured to capture ambient sound around a user, the microphone is configured to capture samples of small segments of the ambient sound, and a speaker;
   an interface having a hardware processor programmed with executable instructions for obtaining input data, transmitting data and providing output data;
   a memory unit storing input information, a library of aversive ambient sound signals, aversive sound feature maps, identifying prediction models, aversive sound identifying classes, and aversive sound suppression prediction models; and
   a processing unit in communication with the earpiece device, the memory unit and the interface and comprising:
      an identifying unit coupled to the earpiece device and the memory unit and programmed with executable instructions to identify an aversive ambient sound signal in the ambient sound segment by extracting at least one feature of the sound in the sound segment, classify such ambient sound segment as a mix-signal of ambient sound segments with aversive sound signal and create a feature map of such sound segment, the feature map of the sound segment is processed using the identifying prediction model stored in the memory unit to compare at least one feature in the feature map with the feature maps of aversive sound signals in the memory unit, wherein when the aversive ambient sound is identified the identifying unit categorizes the aversive sound signal with an identifying class; and
      a filtration processing unit coupled to the identifying unit and the memory unit and programmed with executable instructions to receive the mix-signal of ambient sound segments with aversive sound signal and process the mix-signal computing an amplitude and phase of the mix-signal to generate a feature map of the mix-signal, compare the feature map with the stored feature maps using at least one aversive sound suppressive model and provide a signal of a recommend action through the earpiece device and/or the interface to manage such aversive sound signals.

2. The system of claim 1, wherein the earpiece device further comprises a valve and a first activation device for opening and closing the valve, the valve configured to suppress or isolate the ambient sound segment transmitted to the user.

3. The system of claim 1, wherein the filtration processing unit is further programmed with executable instructions to automatically remove the identified aversive signals from the mix-signal using the generated feature map to obtain a clean sound of the mix-signal which is reconstructed from a frequency domain to a time domain, and combine a phase of the mix-signal with amplitudes of the clean sound for the last segments to create a clean sound signal for transmission to the speaker.

4. The system of claim 3, wherein the filtration processing unit is further programmed with executable instructions to post-process the clean sound signal and generate a smooth clean sound signal.

5. The system of claim 3, wherein the filtration processing unit further comprises a bypass with a gain to create an attenuated aversive sound, the filtration processing unit being programmed with executable instructions to automatically add the attenuated aversive sound signal to the clean sound signal.

6. The system of claim 3, wherein the recommendation action is to remove the identified aversive ambient sound signal.

7. The system of claim 5, wherein the recommendation action is to attenuate the identified aversive ambient sound signal.

8. The system of claim 1, wherein the memory unit further stores a stationary aversive sound suppression prediction model, a non-stationary aversive sound suppression prediction model and a highly dynamic aversive sound suppression prediction model, the filtration processing unit being programmed to access one of the stationary aversive sound suppression prediction model, the non-stationary aversive sound suppression prediction model or the highly dynamic aversive sound suppression prediction model depending on the identified class of the aversive ambient sound signal.

9. The system of claim 1, wherein the processing unit is programmed to record a new identified aversive ambient sound signal to the library of aversive sound signals.

10. The system of claim 9, wherein the library of aversive sound signals comprises user-identified aversive sound signals.

11. The system of claim 1, further comprising an alert system in communication with the interface and/or the earpiece device to generate an alert signal to alert the user of the recommendation action, the alert signal being selected from one of a visual, tactile, sound signal or any combination thereof.

12. The system of claim 2, wherein the first activation device is a button in communication with the earpiece device to manually trigger the valve to suppress or attenuate the aversive ambient sound signal.

13. The system of claim 1, wherein the memory unit further stores pre-recorded sounds to use it for masking the aversive sound signal.

14. The system of claim 13, wherein the filtration processing unit is programmed with executable instructions to automatically add the pre-recorded sound over the mix-signal to mask the aversive ambient sound signal.

15. The system of claim 13, further comprising a second activation device in communication with the earpiece device and the memory unit, the user accessing the stored pre-recorded sounds using the second activation device to play the pre-recorded sound over the mix-signal to mask the aversive ambient sound signal.

16. The system of claim 1, wherein the memory unit is embedded in the earpiece device or positioned remotely from the earpiece device and in communication with the earpiece device and the processor unit by wires, wirelessly or using internet network.

17. The system of claim 1, wherein the processor unit is embedded in the earpiece device or positioned remotely from the earpiece device and in communication with the earpiece device and the memory unit by wires, wirelessly or using internet network.

18. The system of claim 1, wherein the interface is positioned remotely from the earpiece device and in communication with the earpiece device and the processor unit by wires, wirelessly or using internet network.

19. The system of claim 1, further comprising at least one physiological sensor in communication with the processing unit and configured to detect at least one physiological parameter of the user, the processing unit identifying the aversive ambient sound signal in the ambient sound segment if the detected parameter is outside a pre-determined range of the at least one of the detected physiological parameter.

20. The system of claim 19, wherein the identified aversive ambient sound signal is recorded in the library of aversive sound signals.

21. A method for ambient aversive sound detection, identification and management, the method comprising:
capturing an ambient sound around a user using a microphone in an earpiece device, the microphone being used to capture samples of small segments of the ambient sound;
storing input information, a library of aversive ambient sound signals, aversive sound feature maps, identifying prediction models, aversive sound identifying classes and aversive sound suppression prediction models on a memory unit; and
processing the captured sound segments by a processing unit, the processing step comprises:
extracting at least one feature of the sound signal in the sound segment, creating a feature map of the sound segment, comparing the at least one feature in the feature map with the feature maps of aversive sound signals in the identifying prediction model stored in the memory unit, identifying an aversive sound signal in the captured sound segment using the identifying prediction model and categorizing the identified aversive sound signal with an identifying class; and
filtration processing of a mix-signal that comprises the ambient sound segments with the aversive ambient sound signal, computing an amplitude and phase of the mix-signal to generate a feature map of the mix-signal, comparing the feature map with the stored feature maps using at least one aversive sound suppressive model and providing a recommend action to manage the aversive sound signals.

22. The method of claim 21 further comprises obtaining input data from the user, transmitting data and providing output data using an interface having a hardware processor programmed with executable instructions.

23. The method of claim 21, wherein the filtration processing further comprises removing identified aversive signals of the mix-signal to obtain a clean sound of the mix-signal, reconstructing the clean sound from a frequency domain to a time domain, combining a phase of the mix-signal with amplitudes of the clean sound to create a clean sound signal and transmitting the clean sound signal to a speaker.

24. The method of claim 23, wherein the filtration processing further comprises post-processing the clean sound signal and generating a smooth clean sound signal.

25. The method of claim 23, wherein the filtration processing further comprises creating an attenuated aversive sound using a bypass with a gain and adding the attenuated aversive sound signal to the clean sound signal.

26. The method of claim 21 further comprises recording a new identified aversive ambient sound signal to the library of aversive sound signals.

27. The method of claim 21 further comprises storing pre-recorded sounds on the memory unit to use it for masking the aversive sound signal.

28. The method of claim 27 further comprises playing the pre-recorded sound to mask the aversive ambient sound signal.

* * * * *